US008686168B2

(12) United States Patent
Rekker et al.

(10) Patent No.: US 8,686,168 B2

(45) Date of Patent: Apr. 1, 2014

(54) PROCESS FOR THE HYDROGENATION OF FATTY ACIDS USING A PROMOTED SUPPORTED NICKEL CATALYST

(75) Inventors: Tjalling Rekker, Den Ilp (NL); Robert Johan Andreas Maria Terörde, Maarn (NL)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 13/637,088

(22) PCT Filed: Mar. 28, 2011

(86) PCT No.: PCT/NL2011/050209

§ 371 (c)(1),
(2), (4) Date: Dec. 10, 2012

(87) PCT Pub. No.: WO2011/119034

PCT Pub. Date: Sep. 29, 2011

(65) Prior Publication Data

US 2013/0079535 A1 Mar. 28, 2013

(30) Foreign Application Priority Data

Mar. 26, 2010 (EP) .................................... 10158058

(51) Int. Cl.
*C07C 51/36* (2006.01)

(52) U.S. Cl.
USPC .......................................................... 554/146

(58) Field of Classification Search
USPC .......................................................... 554/146
See application file for complete search history.

(56) References Cited

U.S. PATENT DOCUMENTS

| | | | | |
|---|---|---|---|---|
| 4,048,116 | A | 9/1977 | Voges et al. | |
| 5,493,037 | A | 2/1996 | Henderson | |
| 6,054,627 | A | 4/2000 | Thakur et al. | |
| 6,350,923 | B1 * | 2/2002 | Eller et al. | 568/853 |

FOREIGN PATENT DOCUMENTS

| | | | |
|---|---|---|---|
| GB | 384314 | | 11/1932 |
| GB | 384314 | A * | 2/2002 |
| WO | WO-2004/035204 | | 4/2004 |

OTHER PUBLICATIONS

International Search Report in PCT/NL2011/050209,mailed on May 2, 2011, 2 pgs.

* cited by examiner

*Primary Examiner* — Deborah D Carr
(74) *Attorney, Agent, or Firm* — Melanie L. Brown

(57) ABSTRACT

The invention is directed to a process for the hydrogenation of unsaturated fatty acids to produce saturated fatty acids, said process comprising hydrogenating the unsaturated fatty acid in the presence of hydrogen and a supported nickel catalyst, said supported nickel catalyst comprising an oxidic support, 5 to 80 wt. % of nickel, calculated as metallic nickel on the weight of the catalyst, and 0.1 to 10 wt. % of a manganese promoter, calculated as $MnO_2$ on the weight of the catalyst.

19 Claims, No Drawings

PROCESS FOR THE HYDROGENATION OF FATTY ACIDS USING A PROMOTED SUPPORTED NICKEL CATALYST

The invention is directed to a process for the hydrogenation of unsaturated fatty acids to produce saturated fatty acids, said process comprising hydrogenating the unsaturated fatty acid in the presence of hydrogen and a supported nickel catalyst.

Supported metal catalysts are known, and their use in numerous reactions, including the hydrogenation of unsaturated fatty materials, such as oils or fatty acids has been described extensively in the literature. Supported nickel catalysts have been utilized in various hydrogenation processes where low IV (iodine value) fatty products are desired. A low IV is obtained when the product is completely or essentially completely saturated. Since selectivity is irrelevant in fatty acid hydrogenation, the main purpose of the catalyst is to perform the hydrogenation reaction as fast and economically as possible.

U.S. Pat. No. 6,054,627 describes a catalyst comprising the major amount of the oxides of copper or zinc and at least one other metal to be used in hydrogenation reactions. U.S. Pat. No. 5,493,037 describes a catalyst comprising nickel, silica, alumina and one clay mineral binder used in fixed bed hydrogenation of fatty acid. Contents of 10-50 wt. % of nickel are mentioned, without specifying how the weight percentage is defined.

WO 2004/035204 describes a nickel catalyst with magnesium promoter used for hydrogenating unsaturated organic compounds. Contents of 51-80 wt. % of nickel, determined in the reduced catalyst, are disclosed. U.S. Pat. No. 4,048,116 describes an unsupported nickel catalyst also comprising of copper and manganese and optionally molybdenum for hydrogenation of acetylene alcohols. U.S. Pat. No. 6,350,923 describes a process for hydrogenating aldehydes using a supported catalyst consisting of nickel, cobalt or copper and at least one other metal. U.S. Pat. No. 6,350,923 does not describe hydrogenating unsaturated fatty acids using a manganese promoted supported nickel catalyst. Babenkova et al (Kinetics and Catalysis, Vol. 36, No. 2, 1995, pp. 237-240) disclose a manganese doped nickel/kieselguhr catalyst for the hydrogenation of unsaturated triglycerides of sunflower oil fatty acids. GB-A-384 314 describes a process for manufacturing derivatives of soap forming carboxylic acids using first a manganese catalyst and then a nickel catalyst in a two-step catalytic process. GB-A-384 314 does not describe that manganese can be used to promote a nickel catalyst.

Fatty acid hydrogenations can be accomplished generally in a slurry phase with a powdered catalyst or in a fixed bed with a shaped catalyst. Nickel catalysts are often used for fatty acid hydrogenation reactions applications. However, such catalysts may exhibit a relatively fast deactivation caused by extensive crystallite growth as a result of Ostwald ripening and/or by poisoning with catalyst contaminants that are present in the feedstock (e.g. sulphur-, nitrogen- and phosphor compounds). Also major amounts of the nickel dissolve in the fatty acid feedstock under reaction conditions. This deactivation rate should be minimized in order for such a catalyst to be economical in mentioned processes.

The present invention relates to the use of a nickel on silica catalyst which has been promoted with manganese for hydrogenation of fatty acids, which is a feedstock for oleochemical processes.

The invention accordingly is directed to a process for the hydrogenation of unsaturated fatty acids to produce saturated fatty acids, said process comprising hydrogenating the unsaturated fatty acid in the presence of hydrogen and a supported nickel catalyst, said supported nickel catalyst comprising an oxidic support, 5 to 80 wt. % of nickel, calculated as metallic nickel on the weight of the catalyst, and 0.1 to 10 wt. % of a manganese promoter, calculated as $MnO_2$ on the weight of the catalyst.

In the present application, the nickel content in the catalyst composition is calculated as metallic nickel. It is to be noted that normally in a reduced catalyst not all nickel will be completely in metallic state and usually some NiO will be present. Typically, 20-40 wt. % of the total nickel will be present as nickel oxide.

Surprisingly nickel catalysts promoted with manganese have a higher activity under reaction conditions. The actual mechanism for this effect is not known, but it is assumed that the higher activity, despite a lower nickel surface area, is due to a higher turnover number and/or a slower catalyst deactivation.

The fatty acids may be of various origins, e.g. derived from natural oil or originating from tallow or tall oil. The present invention can be applied for the fatty acid hydrogenation to low iodine values, i.e. in the hydrogenation of (poly)unsaturated fatty acids to produce saturated fatty acids.

Fatty acids hydrogenated in accordance with the present invention are carboxylic acids with a branched or unbranched aliphatic chain preferably consisting of $C_6$ to $C_{36}$, more preferably $C_{16}$ to $C_{24}$.

Preferably the catalyst used in the present invention comprises 25 to 60 wt. % of nickel, preferably 30 to 50 wt. %, calculated as metallic nickel on the weight of the catalyst.

The manganese promoter content of said catalyst comprises preferably 0.5 to 6 wt. %, more preferably 1 to 5 wt. %, calculated as $MnO_2$ on the weight of the catalyst.

As support it is preferred to use one or more oxides, whereby of the oxides silica, alumina, silica-alumina, titania, zirconia and combinations thereof are preferred. More in particular it is preferred to use silica as the said oxidic support material. However, other supports are not excluded, for example carbon, zeolites and clay materials.

The most preferred supported catalyst used in the present invention comprises 10 to 94.9 wt. % silica, preferably 34 to 74.5 wt. %, more preferably 45 to 69 wt. %, calculated on the weight of the catalyst.

In a preferred embodiment the supported nickel catalyst comprises 45 to 69 wt. % silica, calculated on the weight of the catalyst, 30 to 50 wt. % of nickel, calculated as metallic nickel on the weight of the catalyst, and 1 to 5 wt. % of a manganese promoter, calculated as $MnO_2$ on the weight of the catalyst.

The catalyst may be coated with a protective layer, e.g. a fatty substance such as hardened soy bean fat, hardened palm oil fat, hardened sun flower oil fat or a combination thereof, which may serve to avoid oxidation of (parts of) the catalyst. A method for applying a suitable fatty is known in generally known in the art, and may be based on WO 2004/035204. This may for example be done by blending a (reduced) catalyst powder into the molten coating material (such as the molten fat) and subsequently solidifying the resulting suspension to form flakes or droplets of coated catalyst particles.

The melting temperature of the protective material with which the catalyst is coated is preferably less than the temperature at which the hydrogenation is carried out, in order to facilitate dissolution of the protective material at the beginning of a hydrogenation process. In particular, when the catalyst is used in a slurry process, the protective coating will preferably dissolve in the feedstock. Else, the coating may be removed from the process, shortly before using the catalyst in a hydrogenation process. The coating may very suitably be removed by contacting the catalyst with a solvent, such as a feedstock, preferably at a temperature higher than the melting point of the coating fat.

The average particle size of the catalyst is preferably from 0.1 to 50 μm. These particles may be shaped (extruded, tabletted, etc.) into larger particles, especially suitable for fixed bed applications.

The nickel surface area of the catalyst (in active form) will preferably have hydrogen adsorption capacity (HAC) of at least 30 ml $H_2$/g Ni, more preferably at least 40 ml $H_2$/g Ni. The nickel surface area as used herein is the value as can be determined by hydrogen desorption in a Micromeretics AutoChem 2920 chemisorption analyzer, after in situ reduction with hydrogen (50 ml/min) for 2 hours at 400° C. Following in situ reduction the sample is cooled to −75° C. with liquid nitrogen. Subsequently, the hydrogen adsorption capacity (HAC) of the sample is determined by measuring the amount of hydrogen that desorbs during heating in a flow of argon (20 ml/min) from −75 to 700° C.

The BET surface area preferably is about 100 to about 450 $m^2$/g catalyst, more preferably about 150 to about 450 $m^2$/g catalyst. The BET surface area as used herein is the value that can be measured by determining the amount of nitrogen adsorbed at 77 K and P/Po of approximately 0.3 and assuming a nitrogen cross sectional area of 16.2 $Å^2$, after degassing the catalyst sample at 180° C.

In a preferred embodiment, the catalyst is made from a catalyst precursor that is prepared by deposition-precipitation, of which it will be clear to the skilled professional how to choose suitable method conditions. In a deposition-precipitation method according to the invention nickel and manganese are precipitated together (i.e. without forming intermediate precipitates of only one or some of the components) on a preformed support that is suspended in the reactor vessel. In such a method, a nickel source and a manganese source may be mixed in a liquid (e.g. water or an aqueous solution) in which the support is suspended, to form a precipitate (a catalyst precursor), comprising all said components, by adding a precipitant, such as an alkaline compound at some stage.

The catalyst precursor is activated by reducing at least part of the nickel content of the catalyst precursor, and optionally the catalyst precursor is calcined before being reduced.

The nickel, silica and manganese sources may be chosen from sources commonly used to prepare catalysts.

Suitable nickel and manganese, and other metal sources include metal salts such as the nitrates, acetates, sulfates, chlorides, etc, most preferably nitrates. Preferably the metal source is a solution of any of these salts.

Suitable silica sources include precipitated silica and diatomaceous earth (kieselguhr). Preferably the silica source is a suspension of any of these components.

The processes of the present invention are performed preferably at a temperature of from 100 to 400° C. Acceptable pressures for the present invention range from 3 to 150 bar.

The process according to the invention has been found to be particularly suitable for the hydrogenation of unsaturated fatty acids to produce saturated fatty acids of low iodine values.

The invention is now elucidated on the basis of some examples, which are not intended to limit the scope of the invention.

EXAMPLES

Example 1 (Comparative)

A non-promoted catalyst was prepared by dosing a 1000 ml nickel chloride solution (82 g/l Ni) into a well stirred vessel (5 liter) containing 2000 ml water into which 100 g silica powder (Crosfield HP250) was dispersed. The temperature was 60° C. and the pH was maintained at 8.0 by intermittently dosing 910 ml of a sodium carbonate solution (225 g/l). The precipitation of the catalyst precursor was completed in 60 minutes.

The catalyst precursor was washed with approximately 30 liters of demineralized water and subsequently filtered and dried overnight in a preheated oven at 110° C. The catalyst precursor was activated by reduction with hydrogen for 2 hours at 400° C.

Example 2

A catalyst was prepared according to the procedure as described in Example 1, except that 15.5 g of manganese chloride ($MnCl_2.6H_2O$) was added to the nickel chloride solution and that 1100 ml of sodium carbonate solution (225 g/l) was used to maintain the pH at 8.0.

Example 3 (Comparative)

A catalyst was prepared according to the procedure described in Example 1, except that 100 g of kieselguhr (Dicalite BP-3) was used as support, that the precipitation was done at 95° C. and that 820 ml of sodium carbonate solution (225 g/l) was used to maintain the pH at 8.0.

Example 4

A catalyst was prepared according to the procedure described in Example 3, except that 15.5 g of manganese chloride ($MnCl_2.6H_2O$) was added to the nickel chloride solution and that 770 ml of sodium carbonate solution (225 g/l) was used to maintain the pH at 8.0.

Activity Test

The activity of the comparative nickel catalysts and the manganese promoted catalysts was determined by hydrogenating 150 g tallow fatty acid having an iodine value (IV) of 56 at 200° C. and a hydrogen pressure of 20 bars with an amount of catalyst corresponding to 0.030 wt % nickel. The time needed to reach an iodine value of 4.0 for the manganese promoted catalysts was compared to that of the comparative catalysts under the same conditions. The hydrogen adsorption capacity (HAC) was determined as previously described and the end IV after 90 minutes was determined using the Wijs method for all four catalysts.

Table 1 shows the results for the silica supported nickel catalysts of Examples 1 and 2.

TABLE 1

| | HAC (ml $H_2$/g Ni) | Time to IV 4.0 (min) | IV after 90 min |
|---|---|---|---|
| Example 1 (comparative) | 65 | >90 | 4.9 |
| Example 2 (manganese promoted) | 53 | 57 | 2.2 |

As can be seen from the above results, the catalyst of the present invention comprising the manganese promoter (Example 2) is more effective in the hydrogenation of the fatty acid (lower iodine value). These results indicate that promoting the catalyst with manganese (Mn/Ni molar ratio of about 0.053) results in a more active catalyst, as expressed by the shorter time needed to reach an iodine value (IV) of 4.0 and the lower iodine value obtained after 90 minutes of hydrogenation.

Table 2 shows the results for the kieselguhr supported nickel catalysts of Examples 3 and 4.

TABLE 2

| | HAC (ml $H_2$/g Ni) | Time to IV 4.0 (min) | IV after 90 min |
|---|---|---|---|
| Example 3 (comparative) | 46 | 86 | 3.7 |
| Example 4 (manganese promoted | 41 | 73 | 2.7 |

Similarly to the results of Table 1, Table 2 shows the same beneficial effect of manganese promotion as demonstrated by Example 4 needing a shorter time to reach an iodine value (IV) of 4.0 and obtaining a lower iodine value after 90 minutes of hydrogenation than the comparative example.

Therefore the use of a manganese promoter has been shown to improve the activity of catalysts for the hydrogenation of fatty acids both consisting of different supports and prepared at different precipitation temperatures.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process for the hydrogenation of unsaturated fatty acids to produce saturated fatty acids, said process comprising hydrogenating the unsaturated fatty acid in the presence of hydrogen and a supported nickel catalyst, said supported nickel catalyst comprising an oxidic support, 5 to 80 wt. % of nickel, calculated as metallic nickel on the weight of the catalyst, and 0.1 to 10 wt. % of a manganese promoter, calculated as $MnO_2$ on the weight of the catalyst.

2. The process of claim 1, wherein the catalyst comprises 25 to 60 wt. % of nickel, calculated as metallic nickel on the weight of the catalyst.

3. The process of claim 1, wherein the catalyst comprises 0.5 to 6 wt. % of a manganese promoter, calculated as $MnO_2$ on the weight of the catalyst.

4. The process of claim 1, wherein the support is an oxidic support, the support selected from silica, alumina, silica-alumina, titania, zirconia and combinations thereof.

5. The process of claim 4, wherein the oxidic support material of said catalyst is silica.

6. The process of claim 1, wherein said catalyst comprises 10 to 94.9 wt. % silica, calculated on the weight of the catalyst.

7. The process of claim 1, wherein the catalyst has an average particle size of 0.1 to 50 μm.

8. The process of claim 1, wherein the catalyst is suspended in droplets, wherein the droplets form a protective coating layer effective in preventing oxidation of the catalyst.

9. The process of claim 1, wherein the hydrogenation is carried out at a temperature between 100 and 400° C.

10. The process of claim 1, wherein the hydrogenation is carried out at a hydrogen pressure between 3 and 150 bar.

11. The process of claim 1, wherein the supported nickel catalyst comprises 45 to 69 wt. % silica, calculated on the weight of the catalyst, 30 to 50 wt. % of nickel, calculated as metallic nickel on the weight of the catalyst, and 1 to 5 wt. % of a manganese promoter, calculated as $MnO_2$ on the weight of the catalyst.

12. The process of claim 11, wherein the catalyst is suspended in droplets, wherein the droplets form a protective coating layer effective in preventing oxidation of the catalyst.

13. The process of claim 1, wherein the hydrogenation is carried out in a fatty acid slurry containing the catalyst.

14. A method of hydrogenating an unsaturated fatty acid, the method comprising hydrogenating the unsaturated fatty acid in the presence of hydrogen and a supported nickel catalyst to form a saturated fatty acid, the supported nickel catalyst including:

an oxidic support;

an amount of nickel present in the range of about 5 to about 80 wt. %, calculated as metallic nickel on the weight of the catalyst; and an amount of a manganese promoter present in the range of about 0.1 to about 10 wt. %, calculated as $MnO_2$ on the weight of the catalyst.

15. The method of claim 14, wherein the supported nickel catalyst wherein the oxidic support comprises silica present in an amount in the range of about 45 to about 69 wt. %, calculated on the weight of the catalyst, the amount of nickel is in the range of about 30 to about 50 wt. %, calculated as metallic nickel on the weight of the catalyst, and the amount of the manganese promoter is in the range of about 1 to about 5 wt. %, calculated as $MnO_2$ on the weight of the catalyst.

16. The method of claim 14, wherein the catalyst is suspended in a protective coating layer of droplets, the protective coating layer being effective to prevent oxidation of the catalyst.

17. The method of claim 16, wherein the protective coating layer comprises a fatty substance.

18. The method of claim 14, wherein the hydrogenation occurs at a temperature in the range of about 100° C. and about 400° C.

19. The method of claim 14, wherein the hydrogenation occurs at a hydrogen pressure in the range of about 3 and about 150 bar.

* * * * *